US005627051A

United States Patent [19]

Duman

[11] Patent Number: 5,627,051
[45] Date of Patent: May 6, 1997

[54] NUCLEIC ACID SEQUENCES ENCODING DENDROIDES ANTIFREEZE PROTEINS

[75] Inventor: John G. Duman, South Bend, Ind.

[73] Assignee: University of Notre Dame du Lac, Notre Dame, Ind.

[21] Appl. No.: 485,359

[22] Filed: Jun. 7, 1995

[51] Int. Cl.$^6$ ............................. C12P 21/02; C07H 21/04
[52] U.S. Cl. ...................... 435/69.1; 536/23.5; 536/24.31
[58] Field of Search ................................ 435/320.1, 69.1; 536/23.5, 24.31

[56] References Cited

PUBLICATIONS

J.G. Duman et al., "Hemolymph proteins involved in insect subzero tolerance: Ice nucleators and antifreeze proteins", In Insects at Low Temperatures, Chapman and Hall (N.Y.), pp. 94–127 (1991).

D.W. Wu et al., "Enhancement of insect antifreeze protein activity by antibodies", Biochem. Biophys. Acta 1076, 416–420 (1991).

J.G. Duman et al., "Adaptations of insects to subzero temperatures", Quart. Rev. Biol. 66, (4) pp. 387–410 (1991).

J.G. Duman et al., "Hemolymph Proteins involved in the cold tolerance of terrestrial arthropods: Antifreeze and Ice Nucleator Proteins". In Water and Life, Springer–Verlag (Berlin), Chapters 17 & 18 pp. 282–315, (1992).

J.G. Duman et al., "Thermal hysteresis proteins". Advances in Low Temperature Biology, vol. 2, pp. 131–182, (1993).

D. Tursman et al., "Cryoprotective effects of Thermal Hysteresis Protein on Survivorship of Frozen Gut Cells from the Freeze Tolerant Centipede *Lithobius forficatus*", Journal of Experimental Zoology, vol. 272, pp. 249–257 (1995).

D.W. Wu et al., "Activation of antifreeze proteins from larvae of the beetle *Dendroides canadensis*", Comp. Physiol. B, vol. 161, pp. 279–283 (1991).

D.W. Wu et al., "Purification and characterization of antifreeze proteins from larvae of the beetle *Dendroides canadensis*", Comp. Physiol. B, vol. 161, pp. 271–278 (1991).

*Primary Examiner*—Dian C. Jacobson
*Assistant Examiner*—Kawai Lau
*Attorney, Agent, or Firm*—Barnes & Thornburg

[57] ABSTRACT

The present invention is directed to nucleic acid sequences encoding *Dendroides canadensis* thermal hysteresis proteins. The THPs of Dendroides have significantly greater thermal hysteresis activity than any other known anti-freeze protein. The thermal hysteresis activity of the purified THPs can be further enhanced by combining the THPs with various "activating" compounds.

4 Claims, 5 Drawing Sheets

Alignment of the Repeat Sequences of Sequence ID Number 1

| Base Pair | | | | | | | | | | | | |
|---|---|---|---|---|---|---|---|---|---|---|---|---|
| 73  | TGT | CAT | GAG | TGT | TAT | GGC | CAA | TGT | ACT | GGT | TCC | GAT |
| 112 | TGT | CGC | TCG | TGT | ACA | GTG | TCT | TGT | ACT | GAC | TGC | CAG | AAC |
| 151 | TGT | CCA | AAT | GCA | CGT | ACA | GCA | TGT | ACT | CGC | TCT | TCA | AAC |
| 190 | TGC | ATT | AAC | GCG | TTA | ACC | *** | TGT | ACG | GAT | TCA | TAT | GAT |
| 226 | TGC | CAC | AAT | GCC | GAA | ACC | *** | TGT | ACT | AGA | TCA | ACC | ATT |
| 262 | TGT | TAT | AAG | GCT | AAA | ACC | *** | TGT | ACT | GGA | TCA | ACC | AAC |
| 298 | TGT | TAC | GAA | *** | GCT | ACA | GCC | TGT | ACC | GAT | TCC | ACG | GGA |

Consensus Sequence $TGT/C$ $C/T X C/T$ $G/A C/A X$ $T/G G/C X$ $X X A/T$ $G/A X X$ $XXX$ $TGT$ $ACX$ $X G/A X$ $T G/C X$ $A/T C/A X$ $\%A \%T$

*FIG. 3*

| | Position 1 | 2 | 3 | 4 | 5 | 6 | 7 | 8 | 9 | 10 | 11 | 12 | 13 |
|---|---|---|---|---|---|---|---|---|---|---|---|---|---|
| Signal Peptide | M | V | W | V | C | K | N | S | I | L | V | I | S |
|  | V | V | L | M | Y | V |  |  |  |  |  |  |  |
| NH₂ Terminus (?) |  |  |  |  |  |  |  |  |  |  |  |  |  |
| Repeat A | C | H | E | C | Y | G | Q | C | T | G | G | S | D |
| B | C | R | S | C | T | V | S | C | T | D | C | Q | N |
| C | C | P | N | A | R | T | - | C | T | R | S | S | N |
| D | C | I | N | A | L | T | - | C | T | D | S | Y | D |
| E | C | H | N | A | E | T | - | C | T | R | S | T | N |
| F | C | Y | K | A | K | T | - | C | T | G | S | T | N |
| G | C | Y | E | A | - | T | - | C | T | D | S | T | G |
|  | C | P |  |  |  |  |  |  |  |  |  |  |  |
| Consensus Sequence | C | X | X | A | X | T | X | C | I | X | S | X | N/D |

FIG. 4

NUCLEIC ACID SEQUENCES ENCODING DENDROIDES ANTIFREEZE PROTEINS

Species from a broad phylogenetic range of insects have been reported to produce thermal-hysteresis proteins (THPs). THPs are believed to play an important role in many plant and animal species' ability to survive exposure to subzero temperatures. By definition, the equilibrium melting and freezing points of water are identical. However, the presence of thermal-hysteresis proteins lowers the non-equilibrium freezing point of water without lowering the melting point (equilibrium freezing point). Thus when THPs are added to a solution they produce a difference between the freezing and melting temperatures of the solution, and this difference has been termed "thermal-hysteresis".

In the absence of THPs a small (about 0.25 mm diameter) ice crystal that is about to melt at the melting point temperature will normally grow noticeably if the temperature is lowered by 0.01° to 0.02° C. However, if THPs are present, the temperature may be lowered as much as 5° to 6° C. below the melting point (depending upon the specific activity and concentration of the proteins present) before noticeable crystal growth occurs. Consequently, because of THPs ability to lower the freezing point of aqueous solutions, they are commonly referred to as antifreeze proteins. THPs lower the freezing point of aqueous solutions via a non-colligative mechanism that does not depress the vapor pressure or raise the osmotic pressure of water, as is the case with colligative type antifreezes such as glycerol.

Anti-freeze proteins are believed to exert their effect by adsorbing onto the surface of potential seed crystals via hydrogen bonding. When anti-freeze proteins adsorb onto the ice surface they interfere with the addition of water molecules and force growth of the crystal into many highly curved fronts with high surface free energy. Consequently, growth of the crystal requires the temperature to be further lowered to allow crystal growth to proceed.

Thermal-hysteresis proteins were first discovered, and have been best studied, in marine teleost fishes inhabiting seas where subzero temperatures occur, at least seasonally. In these THP-producing Antarctic fish an ice crystal present in the blood serum that melts at −1.1° C., will fail to grow in size until the temperature is lowered to −2.5° C. (thermal hysteresis=1.4° C.). Thus the fish is protected from freezing in its ice-laden −1.86° C. seawater environment.

Over the last 15 years it has been demonstrated that many insects and other terrestrial arthropods (including certain spiders, mites, and centipedes) also produce thermal-hysteresis proteins. Low levels of thermal hysteresis activity are also quite common in overwintering plants and are present in certain fungi and bacteria.

Thermal-hysteresis proteins (THPs) have been isolated from four species of insects: *Tenebrio molitor*, the milkweed bug, *Oncopeltus fasciatus*, the spruce budworm, *Choristoneura fumiferina*, and *D. canadensis*. The molecular masses of these THPs range from approximately 14 to 20 kDa. The insect THPs characterized to date do not have a carbohydrate component, nor do they have high percentages of alanine like the type-I fish (flounder) THPs.

The amino acid compositions of representative insect THPs are shown in Table 1, and can be generally characterized as having higher percentages of hydrophilic amino acids (i.e. Thr, Ser, Asx, Glx, Lys, Arg) than the fish THPs, with generally 40–50 mol % of the residues being capable of forming hydrogen bonds.

TABLE 1

Amino acid compositions (mol %) of representative THPs.

| Amino acid | 1 (H-1) | 2 T-4 | 2 T-3 | 3 | 4 |
|---|---|---|---|---|---|
| Asx | 14.3 | 7.3 | 5.3 | 9.5 | 7.1 |
| Thr | 17.2 | 6.6 | 2.3 | 6.0 | 2.7 |
| Ser | 10.3 | 7.4 | 11.1 | 13.0 | 30.5 |
| Glx | 5.2 | 8.9 | 12.4 | 11.0 | 12.3 |
| Pro | 2.6 | 5.9 | 0.0 | 5.0 | 0.0 |
| Gly | 6.6 | 8.3 | 11.4 | 15.0 | 20.0 |
| Ala | 8.4 | 14.3 | 5.0 | 8.0 | 6.8 |
| ½Cys | 15.9 | 0.0 | 28.0 | 6.0 | 0.0 |
| Val | 1.7 | 11.5 | 2.3 | 3.0 | 3.0 |
| Met | 0.2 | 4.8 | 0.0 | 0.0 | 0.0 |
| Ile | 1.5 | 7.1 | 1.0 | 1.2 | 1.9 |
| Leu | 1.9 | 0.0 | 2.2 | 6.5 | 3.1 |
| Lys | 3.4 | 6.8 | 15.4 | 3.1 | 7.5 |
| Arg | 4.8 | 2.6 | 0.0 | 8.0 | 0.0 |
| Tyr | 3.9 | 2.3 | 0.0 | 1.0 | 2.0 |
| Phe | 0.0 | 3.9 | 0.0 | 2.2 | 1.1 |
| His | 1.9 | 1.9 | 3.1 | 0.0 | 2.3 |

1 = *Dendroides canadensis*; 2 = *Tenebrio molitor*; 3 = *Choristoneura fumiferana*; 4 = *Oncopeltus fasciatus*

Several of the insect THPs have significant amounts of cysteine. In particular 16 mole % of the amino acid residues of the THPs of *D. canadensis* are cysteine, approximately half of which are involved in disulfide bridges. Treatment with dithiothreitol, which reduces these disulfide bonds, or alkylation of free sulfhydryls, results in complete loss of thermal-hysteresis activity.

The thermal-hysteresis activity present in the hemolymph (the circulatory fluid of insects) of Dendroides canadensis insects in mid-winter averages 3°–6° C. with some individuals having as much as 8°–9° C. This activity is significantly greater than that which is present in the blood of polar fish; the maximal activity achievable with very high concentrations of the fish THPs is about 1.7° C. FIG. 1 compares the activities of purified THPs from two species of fish and two species of insects: 1=*Dendroides canadensis* THP, the most active THP currently known (solid squares); 2=*Tenebrio molitor* THP (solid circles); 3= activity of the most active fish THP, i.e. Antarctic eelpout and THP of Antarctic nototheniids (open squares); 4= activity of the least active fish THP, from cod *Gadus morhua* (open circles). The maximal activity of the most active fish and *T molitor* THPs are similar, however, the THPs of *D. canadensis* have a greater specific activity and a much greater maximal activity than any other known THP. In addition as will be described later, the *Dendroides canadensis* THPs can be activated by the presence of certain other proteins to produce even greater levels of thermal hysteresis activity.

The present invention is directed to nucleic acid sequences encoding peptides having antifreeze properties, wherein the nucleic acid sequence comprising sequences from a species selected from the genus Dendroides. The activity of Dendroides antifreeze proteins is three to six times greater than those of the fish anti-freeze proteins. Isolation of the nucleic acid sequences encoding these proteins allows the synthesis of the THP proteins in large amounts. Advantageously, these proteins can be used to enhance the supercooling properties of a fluid to prevent the freezing of fluids at temperatures below their equilibrium melting temperature. The proteins can also be used to prevent or limit ice growth or recrystalization of frozen goods, and provide protection from damage that normally would result from freezing biological materials. These effects can be mediated by adding purified THPs alone, or alternatively the THPs can be combined with various "activating" compounds that are known to enhance THP activity.

BRIEF DESCRIPTION OF THE DRAWINGS

FIG. 3 depicts an alignment of the seven repeat nucleic acid sequences of Seq. ID No.: 1.

FIG. 4 depicts an alignment of the seven repeat amino acid sequences of Seq. ID No.: 2 (using IUPAC-IUB single letter amino acid designations). Because the $NH_3$-terminus of the THPs is blocked, the exact starting position of the mature protein has not been confirmed.

DETAILED DESCRIPTION OF THE INVENTION

Figure 1:
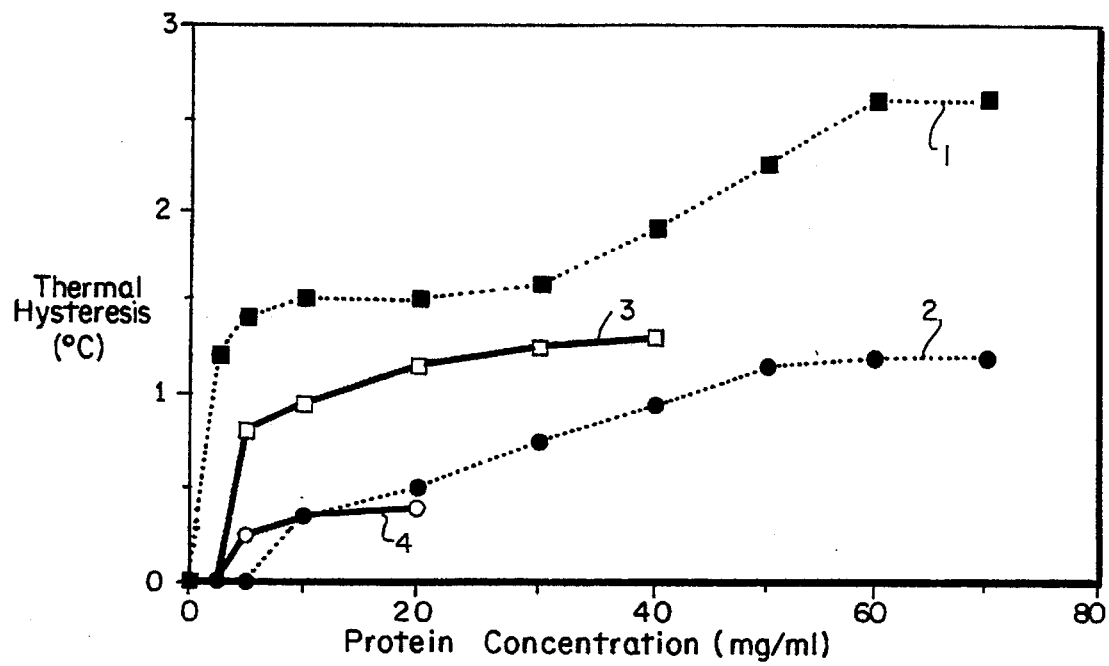
FIG. 1 is a graph illustrating the relative thermal-hysteresis activities of two fish and two insect THPs.

The THPs of *Dendroides canadensis* have significantly greater thermal hysteresis activity than any other known anti-freeze proteins. The maximal activity of purified THPs alone is approximately 2.7° C., whereas the maximal activity of the most active fish anti-freeze protein is only approximately 1.5° C. In addition, certain activator proteins can be combined with the *Dendroides canadensis* THPS to increase the activity of Dendroides THPs to 5°–6° C. Activation of fish THPs has not been demonstrated.

Four THPs have been purified from *D. canadensis* and the amino acid composition of each of the THPs has been determined according to the procedure of Example 1. Table 2 shows that the amino acid compositions (in mole percent) of the four THPs are similar. All four of the proteins have high Cys contents (i.e., ~16 mol %) and approximately half of the Cys residues are involved in disulfide bridges. Hydrophilic amino acids, such as Asx, Glx, Ser, His, Thr, Arg, and Lys comprise 45–55 mol % of the amino acid residues. *Dendroides canadensis* THPs separated by electrophoresis on native PAGE and stained with Periodic Acid-Schiff (PAS) revealed that these THPs are not glycosylated (i.e. the PAS stained gels were negative). In addition, the amino acid analyses did not indicate the presence of amino sugars in any of the Dendroides THPs.

TABLE 2

Amino acid compositions of four Dendroides THPs.
Values are in mole percent. (Tryptophan was destroyed during acid hydrolysis)

|           | H1    | H2    | H3    | H4    |
|-----------|-------|-------|-------|-------|
| Asx       | 14.3  | 13.3  | 12.8  | 15.0  |
| Total Cys | 15.9  | 15.8  | 16.5  | 15.7  |
| (Cystine) | (3.7) | (3.6) | (4.2) | (3.4) |
| Glx       | 5.2   | 5.6   | 4.4   | 7.6   |
| Ser       | 10.3  | 10.0  | 6.5   | 9.5   |
| His       | 1.9   | 2.5   | 0.7   | 2.2   |
| Gly       | 6.6   | 7.1   | 6.4   | 9.3   |
| Thr       | 17.2  | 14.9  | 16.5  | 13.9  |
| Arg       | 4.8   | 4.9   | 1.6   | 1.8   |
| Ala       | 8.4   | 7.8   | 11.6  | 7.9   |
| Tyr       | 3.9   | 3.8   | 4.4   | 2.1   |
| Met       | 0.2   | 0.5   | 0.2   | 0.2   |
| Val       | 1.7   | 2.3   | 4.3   | 3.4   |
| Phe       | 0.0   | 0.0   | 0.5   | 0.6   |
| Ice       | 1.5   | 2.3   | 1.2   | 1.9   |
| Leu       | 1.9   | 2.5   | 2.1   | 2.2   |
| Lys       | 3.4   | 3.2   | 3.6   | 2.9   |
| Pro       | 2.6   | 3.5   | 6.7   | 4.0   |

Even at very high concentrations, the maximal activity of purified THPs (about 2.7° C.) is significantly less than that seen in the hemolymph of *D. canadensis* species in midwinter. The population mean thermal hysteresis (freezing point–melting point) activity of Dendroides hemolymph ranges from 3° to 6° C., with some individuals having hysteresis activities as high as 8° to 9° C. Running the assay at the optimal pH (~7.8) and addition of inorganic ions or polyols increases activity slightly, however, the activity is still considerably less than that seen in winter hemolymph. A clue to this dilemma was provided by noting the effect specific antibodies raised against THPs had on thermal hysteresis activity.

Surprisingly, the addition of specific polyclonal antibodies to the purified *D. canadensis* THPs was found to substantially increase thermal-hysteresis activity of the THPs. Addition of 0.5% (v/v) antiserum to aqueous solutions of THP above about 3 mg/ml resulted in a doubling of activity. At slightly lower THP concentrations where thermal-hysteresis activity was not detectable, activities of 1.5° to 2.5° C. were achieved with antibody addition. Similar increases in activity were produced with T molitor THPs upon addition of a specific antibody.

One explanation for this enhanced THP activity upon addition of specific antibodies is based on the assumption that THPs bound to IgGs are still able to hydrogen bond to ice crystals. If this is the case, then a THP-IgG complex will block a larger surface area of the seed crystal than a single THP molecule alone (the molecular mass of IgG is about 150 kDa while and that of the THPs is about 8 kDa). If this explanation for the enhancing effect of the antibody addition is correct, then one would predict that addition of goat-anti-rabbit IgG to the solution of the THPs plus rabbit anti-THP IgG should increase activity even more, because the complex of THP plus rabbit anti-THP IgG plus goat anti-rabbit IgG antibody should block an even larger surface area of the ice crystal. Experimental data has shown that the addition of goat anti-rabbit IgG antibody to the solution of the THPs plus rabbit anti-THP IgG did result in an additional enhancement of thermal-hysteresis activity.

Thus the activity of the *D. canadensis* THPs can be enhanced or "activated" by another protein present in the insect hemolymph that is capable of binding to the THP. To determine whether a particular protein or other macromolecule could activate the Dendroides anti-freeze protein, the thermal hysteresis activity of an anti-freeze preparation was measured with and without the potential activator as described in Example 2.

To isolate additional factors that enhance thermal hysteresis activity in the hemolymph, hemolymph protein fractions (from a gel filtration column) that lacked thermal-hysteresis activity were systematically added to an aqueous solution containing a low concentration of THPs (4 mg/ml).

Most fractions had no effect on activity (i.e. LIB), but one particular fraction greatly enhanced activity to 5.24° C. (See Table 3, #2). The activating protein present in this fraction was purified. It has a molecular mass of 70 kDa and had been designated as the endogenous THP-activator protein.

TABLE 3

Effects of addition of various proteins on activity of a solution of THPs (4 mg/ml) from *D. canadensis*[a]

| Addition | Thermal Hysteresis (°C.) | Thermal Hysteresis Activity increase (°C.) |
| --- | --- | --- |
| (1) None | 1.60 | 0 |
| (2) Other *D. canadensis* hemolymph protein (non-THP) fractions; | | |
| LIB | 1.52 | 0 |
| THP-Activator | 5.24 | 3.64 |
| (3) Gelatin (5 mg/ml) | 3.13 | 1.53 |
| (4) Tipula ice-nucleator proteins: | | |
| LPIN (1 mg/ml) | 3.49 | 1.89 |
| PIN (1 mg/ml) | 3.98 | 2.38 |
| (5) Tipula PIN (1 mg/ml) + gelatin (5 mg/ml) | 5.80 | 4.20 |
| (6) Antiserum (0.5%) | 3.18 | 1.58 |

Interestingly, the endogenous THP-activator protein has ice-nucleator activity (as determined by the assay described in Example 2). Other insect ice-nucleator proteins and a lipoprotein ice-nucleator (from the freeze-tolerant cranefly *Tipula trivitta*) were also assayed for the ability to activate the *D. canadensis* THPs (See Table 3, #4). Although these proteins were not as efficient as the endogenous THP-activator protein, they did provide significant enhancement, increasing activity from 1.60° C. in their absence to 3.0°–4.0° C. when present. Thus it is anticipated that all ice-nucleator proteins will function as effective enhancers of THP thermal-hysteresis activity. Low concentrations of gelatin or agar (below that needed for a gel state) also were activators.

A modified Western blotting procedure was used to demonstrate that the activator proteins bind to the THPs. The activator was run on an electrophoresis gel and transblotted to nitrocellulose paper (or spotted on nitrocellulose paper directly), and the paper incubated in a solution containing the THPs, to allow the THPs the opportunity to complex to the activator, which was immobilized on the nitrocellulose. The solution of THPs was removed, the nitrocellulose paper washed, and then incubated with anti-THP rabbit antiserum, followed by goat-anti-rabbit IgG labeled with horseradish peroxidase antiserum to detect the presence of THPs. In every instance, the activators were shown to bind to the THPs or vice versa.

The enhancement of thermal-hysteresis activity by ice-nucleator proteins, including the endogenous activator protein, and the demonstration that these activators complex with the *D. canadensis* THPs suggested that in the process of binding to these ice-nucleators the THPs may inactivate the ice nucleators. This has now been demonstrated.

Figure 2:
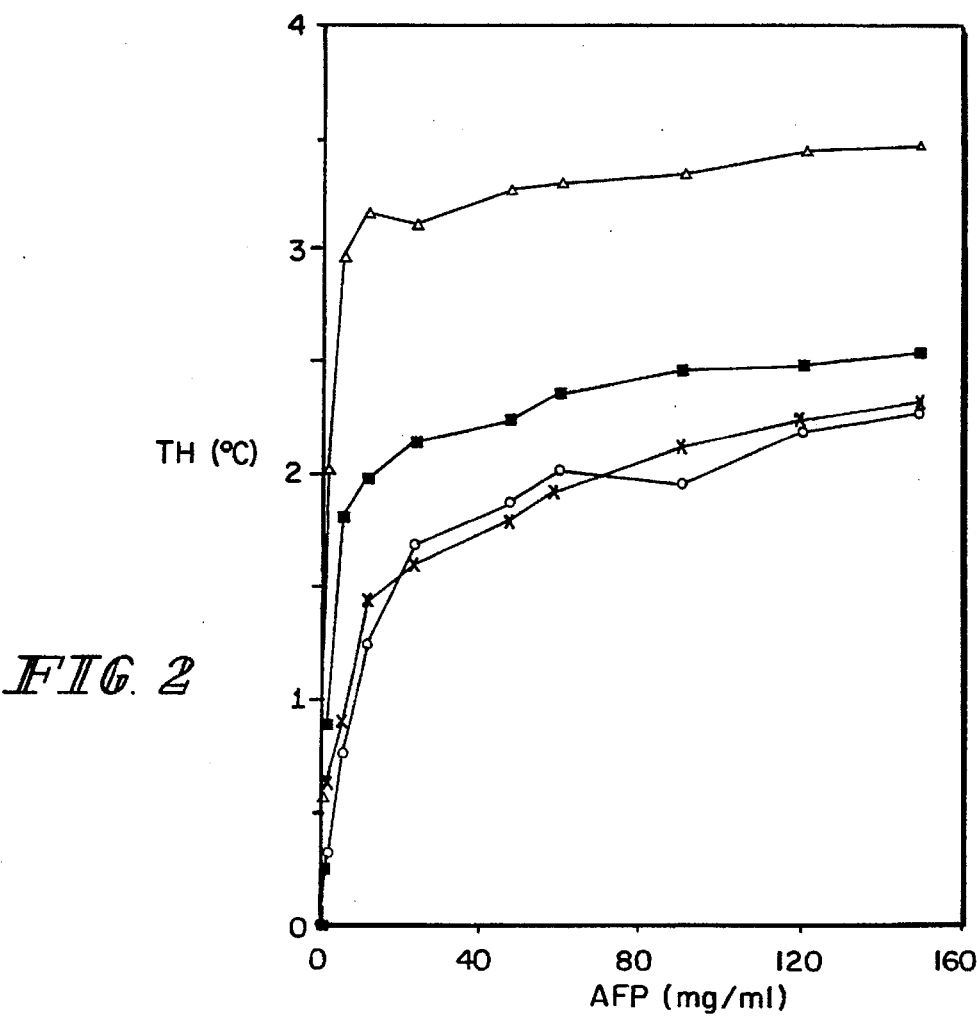
FIG. 2 is a graph illustrating the enhanced thermal-hysteresis effect of combining different *Dendroides canadensis* THPs at various concentrations.

In addition to the enhanced activity induced by the presence of ice-nucleator proteins, the combination of the different THPs present in *D. canadensis* hemolymph provides a synergistic effect. At least four similar THPs are present in the winter hemolymph of *D. canadensis*. When two THP fractions, one comprising THPs $H_1$ and $H_2$ and the other comprising THPs $H_3$ and $H_4$ are combined, the resulting mixture has greatly increased thermal-hysteresis activity. FIG. 2 summarizes data showing the effect of combining four different *Dendroides canadensis* THPs at various concentrations on thermal-hysteresis activity: (open circles represent THP $H_3$ alone; X's represent THP $H_4$ alone; solid squares represent a combination of $H_3$ and $H_4$; and open triangles represent a combination of $H_1$, $H_2$, $H_3$ and $H_4$).

*D. canadensis* THP fractions 6A and 6B (representing $H_1/H_2$ and $H_3/H_4$, respectively) separately have thermal-hysteresis activity of 1.60° C. when present at a concentration of 2 mg/ml. However when these two fractions are mixed together the resulting mixture has a 3.30° C. thermal hysteresis value. This level of thermal hysteresis activity is not achieved by doubling the concentration of either fraction alone.

In summary, it appears that the high levels of thermal hysteresis in *D. canadensis* hemolymph in winter result from (a) increased concentrations of THPs, (b) the combination of the four, perhaps more, THPs, and (c) the enhancement of activity by the endogenous activator protein.

Genes encoding *D. canadensis* THPs have now been isolated and characterized. The DNA sequences encoding the dendroides THPs were isolated from a *D. canadensis* expression cDNA library using techniques familiar to those skilled in the art. The THP encoding genes were identified by antibody screening using anti-Dendroides THP rabbit Serum.

These cloned Dendroides THP genes can be inserted into commercially available DNA vectors (expression vectors) to express the encoded gene protein product. These expression vectors have promoter sequences and other regulatory sequences necessary for expression in host cells. The technique of using expression vectors to introduce exogenous genes and express their protein products in a host cell is well known to those familiar with the art. For example the expression vector pET21a is commercially available and can be used to express proteins in *E. coli*. Alternatively the protein can be expressed in a eukaryotic cell, such as yeast, using Pichia expression vectors (i.e. pHIL-D2) commercially available from Invitrogen. The Baculovirus system is also commercially available and can be used to express the THP genes in insect cultures.

Once the THP gene or fragment thereof has been subcloned into an expression vector, the resulting vector can be used to transform a host cell, using procedures known to those familiar with the art. Such transformation procedures include but are not limited to microinjection, mircoprojectile bombardment, electroporation, calcium chloride premeablization, polyethylene glycol permeabilization, protoplast fusion or bacterial mediated mechanisms such as *Agrobacterium tumafaciens* or *Agrobacterium rhizogenes*.

Host cells may be selected from any cell in which expression of modified proteins can be made compatible, including bacteria, fungus, yeast, plant cells and animal cells. Suitable host cells include prokaryotes selected from the genus Escherichia and eukaryotes selected from the genus Pichia. The transformed host cells will synthesize the modified protein which can be isolated and purified using standard methods known to those familiar with the art. One embodiment of the present invention comprises a method for using a host cell transformant, having heterologous DNA sequences encoding a Dendroides antifreeze protein, to produce a protein having antifreeze properties. The method comprises the step of culturing the cell transformant under conditions conducive to the expression of the antifreeze protein.

In accordance with one embodiment of the present invention, THP genes are inserted into vectors and used to transform plant cells using techniques known to those skilled in the art. These transformed plant cells can then be used to regenerate an entire plant or seed that expresses Dendroides THP proteins. Thus a plant entity consisting essentially of a plant cell, seed or plant can be produced from the in vitro introduction of DNA sequences encoding one or more Dendroides antifreeze proteins into plant cells. It is anticipated that the expression of the anti-freeze proteins in the cells of transgenic plants will enhance their resistance to freezing temperatures and decrease frost damage to plants exposed to freezing temperatures. Similar techniques known to those skilled in the art can be used to generate other transgenic animals.

Two THP genes have been sequenced and the nucleic acid sequence of these two genes is represented by Seq ID No: 1 and Seq ID No: 3 respectively. Initiation codons for the two sequenced THP genes are located at positions 16 and 22 and stop codons are located at positions 340 and 349 of Seq ID No: 1 and Seq ID No: 3, respectively. These two genes are very similar in sequence to one another; there are only a total of 8 single base pair differences and a single 3 base pair deletion in the coding sequence of Seq ID No: 1 relative to Seq ID No: 3 making the two sequences over 95% identical in sequence.

Each of the two Dendroides THP genes (Seq. ID No: 1 and Seq ID No: 3) contain a 39 base pair sequence and a 36 base pair sequence that are repeated four times and three times, respectively, within the coding portion of the THP gene. When the repeat sequences are aligned, as indicated in FIG. 3, a consensus sequence can be generated that is representative of the repeat portions. The consensus nucleic acid sequence for the 39 base pair repeat is:

TGYYNYRMNK SNNNWRNNNN NTGTACNNRN TSNWMNRWY (Seq ID No: 5)

and the consensus nucleic acid sequence for the 36 base pair repeat is:

TGYNNNAANG CNNNAACNTG TACNNRNTCA WMNRWY (Seq ID No: 6)

wherein A is adenine, C is cytosine, G is guanine, T is thymidine, Y is cytosine or thymidine, R is adenine or guanine, M is adenine or cytosine, K is guanine or thymidine, S is guanine or cytosine, W is adenine or thymidine and N is adenine, cytosine, guanine or thymidine.

The protein sequence of the two sequenced Dendroides THP genes has been determined empirically and is represented by Seq ID No: 2 and Seq ID No: 4 respectively. The first 19 amino acids of the deduced amino acid sequence represent a signal peptide that is cleaved from the mature protein. The two protein sequences are very similar; the mature proteins have only two differences. An Asparagine (Asn) is substituted for an Isoleucine (Ile) at amino acid 60 and an additional Threonine (Thr) is inserted in Seq ID No: 4 relative to Seq ID No: 2 at amino acid 100.

Direct sequencing of protein fragments has also been conducted. Two fragments have been sequenced. The first fragment was a 57 amino acid sequence that matched identically to a 57 residue region from the derived protein sequence of the nucleic acid Seq ID No: 1. A second peptide of 28 amino acids has also been sequenced (Seq ID No: 7), and compared to the 57 amino acid sequence. Direct comparison of the 28 amino acid sequence to the amino acid sequences of Seq ID No: 2 and Seq ID No: 4 revealed a total of seven differences over the 28 residue region relative to either Seq ID No: 2 or Seq ID No: 4. Thus the 28 amino acid sequence is likely encoded by one of the Dendroides THP genes that has not yet been isolated. However, using techniques known to those skilled in the art, knowledge of the amino acid sequence of the 28 amino acid peptide enables the construction of probes for isolating the gene encoding the THP that correlates to the peptide fragment.

Examination of the derived protein sequences of Seq ID No: 3 and Seq ID No: 4 reveal an amino acid repeat sequence in the Dendroides anti-freeze proteins. Based on these two sequences an amino acid consensus sequence, as represented by Seq ID No: 8, can be derived that is representative of the thirteen amino acid repeat sequence. The repeat sequences of the two amino acid sequences (Seq ID No: 2 and Seq ID No: 4) has been aligned as shown in FIG. 4 to indicate the thirteen amino acid consensus sequence. Positions 1, 8, and 9 are completely conserved throughout all the repeat sequences and represent a cysteine, cysteine and threonine amino acids respectively. Positions 4, 6, and 11 are also highly conserved and are generally alanine, threonine and serine, respectively. The thirteenth position is generally either aspartic acid or asparagine. Throughout much of the THP proteins every sixth amino acid is cysteine.

Three of the repeat sequences (repeats D, E and F) of Dendroides anti-freeze proteins Seq ID No: 2 and Seq ID No: 4 comprise a repeat sequence of only 12 amino acids. Based on these three repeat sequences an amino acid consensus sequence, as represented by Seq ID No: 9, can be derived that is representative of the twelve amino acid repeat sequence.

It is anticipated that an artificial gene could be synthesized that would encode a protein having either the 13 amino acid consensus repeat (Seq ID No: 8) or the 12 amino acid consensus repeat (Seq ID No: 9) or a combination of the two. The protein encoded by this gene would be expected to have anti-freeze properties similar to the natural Dendroides THPs.

Advantageously, information generated from the sequencing of the THP proteins and their respective genes allows portions of the genes to be used as probes for detecting additional THP genes. In one embodiment the probe comprises nucleic acid sequences at least ten nucleotides long, more particularly, longer than 20 nucleotides. The portion of the THP gene utilized for a probe is selected from a region of the THP gene that is highly conserved, to ensure detection of all THP genes. Nucleic acid probes derived from Dendroides THPs can also be used to identify additional THPs from other organisms that have similar high thermal-hystersis properties. Isolation of additional THP genes from Dendroides, or other freeze avoiding or freeze tolerant species, can be accomplished by labelling the nucleic acid probe and hybridizing the probe with a genomic or cDNA library using techniques know to the skilled practitioner.

THPs are also believed to play an important role in allowing organisms to survive freezing of their extracellular fluids. Organisms that can survive freezing are referred herein as "freeze tolerant" organisms to distinguish them from "freeze avoiding" organisms (which survive subzero temperatures by preventing freezing). Some freeze tolerant arthropods and plants produce THPs in winter but usually the level of thermal hysteresis activity is lower in freeze tolerant species than that typically seen in freeze avoiding species. For example, the centipede *Lithobius forficatus* produces THPs, but too little thermal hysteresis activity is present to provide significant antifreeze protection. However, *L. forficatus* are freeze tolerant, and thus even if freezing is initiated across the cuticle from external ice, the organism can still survive temperatures at least as low as −6° C.

To test THPs' ability to protect cells from freeze damage, *L. forficatus* cells were frozen at various temperatures and then thawed, either with or without the addition of *Dendroides canadensis*' THPs, and the survival of the cells evaluated. The cells tested were isolated from the midgut of both winter and summer collected *L. forficatus*. (See example 3)

The addition of THPs increased the survival of cells from freeze damage and in particular a THP concentration between 0.02 mg/ml ($2.4 \times 10^{-6}$M) and 0.20 mg/ml ($2.4 \times 10^{-5}$) was determined to be optimal. It is noted that high concentrations of THP actually reduce cell survival upon freezing; a THP concentration of 2 mg/ml results in zero percent survivorship. The presence of THPs (0.02 mg/ml) in the bathing medium produced a statistically significant increase in cell survival, indicating a cryoprotective function for the THPs. The $LT_{50}$ (temperature of 50% survival) of cells isolated from centipedes collected in the summer was shifted from $-8.2°$ C. to $-15.0°$ C., and the $LT_{50}$ of cells isolated from centipedes collected in the winter was shifted from $-12.1°$ C. to $-15.1°$ C. by addition of (0.02 mg/ml) THPs. Also, cells from summer collected centipedes which had been incubated in media containing THPs, then washed in buffer to remove the protein from the media prior to freezing, demonstrated significantly increased survivorship after freezing ($LT_{50}=-14.5$).

The presence of THPs in the medium also provided some protection to cells frozen under conditions designed to promote the potentially damaging process of recrystallization (See FIG. 5). To induce recrystalization, preparations of cells were frozen in the presence of 2 mg/ml THP (fraction 6B, see example two) at $-14°$ C., held for ten minutes, then raised to $-6°$ C. and held at this higher temperature for an additional 30 minutes before being thawed and their survival evaluated. A control freezing treatment without thermal hysteresis protein was conducted simultaneously with the test sample to allow direct comparison of THP induced cell freeze resistance. This procedure is similar to that used previously to demonstrate that winter centipede hemolymph contains recrystallization inhibition activity (Tursman et al, '94) The survival rates of cells frozen without THPs under conditions designed to promote recrystalization are lower than the survival rates of cells frozen and held at a constant temperature of either $-6°$ or $-14°$ C. and then quickly thawed (See Table 4). *L. forficatus* gut cells, either with or without THPs, were frozen under conditions designed to promote recrystallization (treatments E and F), freezing initially at $-14°$ C. for 10 minutes and then raising the temperature to $-6°$ C. for an additional 30 minutes. Control cells (treatments A–D) were held at either $-14°$ or $-6°$ C. for either 10 or 40 minutes. As the data in Table 4 indicate, the presence of THPs in low concentrations greatly enhanced the survival of cells frozen under conditions that promote recrystallization.

TABLE 4

Survivorship of *L. forficatus* gut cells frozen under conditions designed to promote recrystallization

| Season of Collection | Freezing Temperature (°C.) | Freezing Time (Min.) | % Survivorship (−)THPs | % Survivorship (+)THPs |
|---|---|---|---|---|
| A) Summer | −14 | 10 | 18.3 | 48.0 |
| B) Summer | −14 | 40 | 18.9 | 45.1 |
| C) Summer | −6 | 10 | 68.3 | 87.9 |
| D) Summer | −6 | 40 | 65.9 | — |

TABLE 4-continued

Survivorship of *L. forficatus* gut cells frozen under conditions designed to promote recrystallization

| Season of Collection | Freezing Temperature (°C.) | Freezing Time (Min.) | % Survivorship (−)THPs | % Survivorship (+)THPs |
|---|---|---|---|---|
| E) Summer | −14 ↓ −6 | 10 ↓ 30 | 7.4 | 36.7 |
| F) Winter | −14 ↓ −6 | 10 ↓ 30 | 15.4 | 41.7 |

Cell preparations were also pretreated with thermal hysteresis protein and then the protein was removed from the bathing medium prior to freezing to determine if the THP antifreeze properties can be mediated through binding to cell membranes or internalization of the THPs. *L. forticatus* cells pretreated with THPs and washed prior to freezing showed enhanced survival after freezing.

Immunofluorescent photomicrographs were prepared for cell preparations collected from both winter and summer centipedes and either treated, or left untreated, with THPs. Untreated cells (not exposed to THPs) from animals collected in summer show very little fluorescence (presumably autofluorescence) while those treated with Dendroides THPs, and then rinsed, immunofluoresce strongly, indicating that the protein has adhered to the surface of the cells and/or has possibly been incorporated into the cells. Cells harvested from species collected in the winter, and not treated with THPs, still immunofluoresced, suggesting the natural occurrence of THPs in and/or on the centipede cells in winter. The trypsin treatment used in the isolation of these cells could be expected to cleave exposed proteins on the surface of membranes. Yet sufficient THP remains on the winter cells to interact with the anti-THP antibody.

Thus immunofluorescence studies of cells treated with THPs indicated that the THPs were present in the cells and/or on the cell membrane. This implies that membrane bound, or possibly intracellular, THPs provide protection.

EXAMPLE 1

Purification of *Dendroides canadensis* THPs

Collection of larvae. Larvae of *Dendroides canadensis* were collected periodically from late fall to early spring from under the loose bark of dead trees near South Bend, Ind., USA. Larvae were held at 4° C. in containers with partially decomposed wood from oak logs, until they were processed.

Purification. Both hemolymph and whole bodies were used as the starting material. Hemolymph was obtained from the Dendroides larvae by puncturing the larvae in the dorsal midline with a 28-gauge needle and collecting the hemolymph (approximately 5 μl per larva) in a 10 μl glass microcapillary via capillary action. The pooled hemolymph was frozen at −30° C. After bleeding, the larvae were frozen at −30° C. until processed. Purification from hemolymph. Step 1: Ultrogel AcA-54 gel filtration chromatography. Dendroides hemolymph (2–3 ml) was applied to an Ultrogel AcA-54 (IBF Biotechnics, Inc.) column (1.9×120 cm.). The eluting buffer was 0.025M TRIS (pH 7.5), 0.1N NaCl at a flow rate of 5 ml/hr (tube volumes collected were 2.2 ml). Elution of protein fractions was monitored at an absorbance of 230 nm. Tubes representing protein peaks were pooled, concentrated by freeze drying, redissolved in water, dialyzed exhaustively against distilled water to remove salts, freeze-dried a second time and redissolved. Each protein fraction was then assayed for antifreeze activity according to the melting point-freezing point difference (thermal hysteresis) method of DeVries [*Methods in Enzymology*, Vol. 127, p. 293–303(1986)]. The active fractions were usually rechromatographed through a second, smaller (1.4×110 cm) Ultrogel AcA-54 column.

Step 2: Reversed-phase HPLC ultrasphere ODS column. Two active fractions were separated from the AcA-54 column, designed 6A and 6B. These were further separated on reversed-phase high pressure liquid chromatography (HPLC), using an ultrasphere C18 column (Rainin), 5 µm, 4.6 mm (ID) ×25 cm (L) equipped with a guard column of the same stationary phase. The columns were equilibrated with 0.1% trifluoracetic acid (TFA) in $dH_2O$. The proteins were eluted over a 60-min period with a 20–26% linear gradient of acetonitrile with 0.1% TFA at a flow rate of 1 ml/min. Elution of protein peaks was monitored at an absorbance of 220 nm. Peak eluant fractions were freeze dried, redissolved in distilled $H_2O$ and checked for thermal hystersis activity.

Purification from whole larvae. Whole larvae were homogenized in 50% ethanol at 4° C. and centrifuged at 11.220×g at 4° C. for 15 min. The supernatant was dialyzed (Spectrapor, 2500 MW cutoff) against 25 mM TRIS-Cl buffer (pH 9.0) and chromatographed on a DEAE-Sepharose CL-6B (Pharmacia) (2.5×20 cm) ion-exchange column. Fractions were eluted using stepwise increases in NaCl (tube volumes were 6 ml). Active fractions were subsequently run on gel filtration (Ultragel AcA-54), followed by HPLC as described above for purification from the hemolymph.

Polyacrylamide gel electrophoresis (PAGE). Native and SDS-PAGE were performed as criteria of purity using the technique of Ornstein (1964) and Laemmli (1970). BIO-RAD low range molecular weight markers were used in the SDS-PAGE. The gels were usually stained with Coomassie blue (Fairbanks et al. 1971). Periodic acid-Schiff stain was used to determine whether the proteins might contain carbohydrate (Kapitany and Zebrowski 1973).

Amino acid analysis. Purified THP (0.1 mg) was hydrolyzed in 5.7N HCl for 24 h at 110° C. Amino acid analyses were done on a Beckman Model 117 amino acid analyzer and on a Waters Picotag System. The analyses provided by the two systems were essentially identical except that the former provided the total cysteine contribution while the latter gave only cystine. Thus, a comparison of the two yielded total cysteine, cystine and free cystine components of the proteins.

EXAMPLE 2

Assay for Measuring THP Activation

An aqueous solution of the potential activator was mixed (1/1 volume/volume) with an 8 mg/ml solution of anti-freeze protein (final concentration of anti-freeze protein equal to 4 mg/ml of a mixture of two Dendroides anti-freeze proteins, $H_3$ and $H_4$). A mixture of the two anti-freeze proteins ($H_3$ and $H_4$) in deionized water at 4 mg/ml was used as a control. After incubation of the mixtures at room temperature for 15 minutes, thermal hysteresis was measured using the capillary-melting point technique of DeVries [*Methods in Enzymology*, Vol. 127, p. 293–303(1986)]. Measurements were made a minimum of three times on each sample. The effectiveness of activation by the added substance was determined with one-way ANOVA and Turkey's test.

Measurement of Ice Nucleator Activity

To determine whether certain proteins have ice nucleator activity the effect of addition of the protein on the supercooling point (nucleation temperature) of a buffer solution was determined by a droplet technique [Zachariassen et al., *Cryobiology*, 19:180–184 (1982)], using droplets of 1 µl volume. Addition of a protein with ice nucleator activity causes a statistically significant increase in supercooling point of the buffer solution.

EXAMPLE 3

Dendroides THP Cryoprotective Capabilities

Cell Preparation.

*L. forticatus* centipedes were collected from woodland habitats in Porter County, Ind. (northwestern Indiana) in both winter and summer. Cells were isolated from the gut in the following manner. Guts were dissected free from other tissues through a dorsal midline incision in the cuticle. The middle portion of the gut was used, after the gut contents and the Malpighian tubules were removed. To remove the gut contents, the gut tube was grasped at one end with fine forceps, wrapped several times about a 20 gauge hypodermic needle shaft, and slowly pulled perpendicular to the needle, squeezing out the contents. After rinsing in phosphate buffered saline (PBS, 0.9% NaCl, w/v; pH=7.4) the tissue was immersed in 0.5 ml of a trypsin solution (15–20 units of activity/ml) in a small centrifuge tube and minced with fine scissors. This preparation was held at room temperature for a period of 20 minutes with occasional gentle agitation.

The minced sample was centrifuged at 1000 g for one minute, and the supernatant discarded. The remaining cellular pellet was resuspended in PBS, respun and the supernatant was decanted. The pellet of cells were then resuspended in 100 µl of PBS containing 0.2% Trypan Blue. This stock suspension was held in an ice bath at 0° C. Aliquots of 15 µls were removed and the cells either counted directly in a hemocytometer chamber as controls, or subjected to the various freezing treatments described below and then counted, and their viability determined (see below) using a microscope at 440×power. Cells taken from 2 or 3 individual centipedes were pooled to determine survivorship at each experimental temperature.

Variables such as trypsin activity, digestion times, and optimal holding times and conditions were evaluated. Warmer (30° C.) digestion temperatures and longer exposures to trypsin digestion (greater than 20 minutes) lowered survival considerably.

The percentage of live cells in the preparation (held at 0° C.) decreased slowly in a linear manner over time, but survivorship was typically still above 90% after 3–4 hours exposure to 0° C. This linear decrease in survivorship of the stock cells held at 0° C. was used to provide the correction factor explained below.

Freezing Procedures.

Hemolymph from winter collected *D. canadensis* larvae was applied to an AcA-54 gel filtration column, and two fractions with thermal hysteresis activity were separated (6A and 6B). Although each of these fractions migrates as a single band on either native or SDS-PAGE, these two fractions can be further fractionated, by reversed-phase HPLC, into several additional fractions, all of which have thermal hysteresis activity. Fraction 6B, without HPLC separation, was used in the centipede cell freezing experiments.

*D. canadensis* THPs were added to suspensions of *L. forficatus* cells in PBS. Controls were frozen either in PBS alone, or in PBS containing bovine serum albumin (BSA) at appropriate concentrations. 15 µl of each sample was pipetted onto a glass coverslip and placed on a cold plate precooled to a predetermined temperature in an insulated chamber. Spontaneous freezing (visually observable) of the sample usually occurred between −2° and −4° C., however, if this did not occur the sample was seeded with an ice crystal at −5° C. The sample was held at the test temperature for 10 minutes, after which coverslips were lifted from the plate with forceps and quickly thawed on a fingertip.

After freezing and thawing, the cells were pipetted into a hemocytometer where they were observed and counted. Whole, unstained, refractile cells were considered to be living while nonrefractile cells that had taken up the Trypan Blue stain were counted as dead. The percentage of total cells living was recorded as the raw score for the treatment being evaluated. Typically, 300–700 cells were counted per sample.

The percentage of live cells in the stock suspension (PBS containing 2% Trypan Blue) decreased slowly over time, and this decreased cell viability was used to correct the raw score of cells surviving the various freezing treatments. The number of viable cells in the stock suspension of cells was obtained at the start and the end of each trial (to determine the rate of cell death), and a correction factor was applied to each test result to compensate for the decline in living cells. The percent decline per minute was multiplied by the elapsed time (time elapsed from preparation of the stock suspension of cells and time of freezing) and this number was subtracted from the initial number of viable cells to calculate the correction factor. The raw score (total number of viable cells after freezing) was divided by this factor to give the corrected score for that particular treatment. For example if an initial cell suspension of 1000 cells were prepared and one cell died per minute in the stack suspension of cells (1% decline per minute) and a test sample was tested 5 minutes after initial preparation of the stock suspension of cells, the correction factor would be 1000−(1×5)=995. The number of living cells in the test sample after freezing would then be divided by the correction factor (995) to obtain the correct score.

The corrected score reflects an estimate of the percentage of cells surviving a given treatment if 100% of the treated cells had been viable prior to freezing. This correction factor was necessary to allow comparison of treatments done at different times after preparation of the cells. Statistical evaluation of the cell freezing data was performed using a linear regression analysis of covariance (ANCOVA).

THP/cell Membrane Interaction

To determine whether THPs might interact directly with the cell membrane or perhaps be incorporated into the cell preparations were pretreated with thermal hysteresis protein and then the protein was removed from the bathing medium prior to freezing. Cells were suspended in a PBS solution of THP protein at 0.06 mg/ml and held for 30 minutes at 0° C. The cell preparation was then centrifuged, the supernatant decanted, the cells resuspended in PBS (without thermal hysteresis protein) and centrifuged again. This rinsing procedure was repeated a second time. After decanting the supernatant, the cells were suspended in PBS containing Trypan Blue as previously described, and subjected to the freezing trials reported.

Immunological analysis of THP/cell interaction.

To determine if *L. forficatus* THP is immunologically similar to that of the beetle *Dendroides canadensis*, immunoblots (slot blots) of centipede hemolymph were probed with anti-Dendroides THP antiserum. Cross reaction of the anti-Dendroides THP antiserum with centipede hemolymph suggests common epitopes between the Dendroides and centipede THPs. Samples (2 µl) of centipede hemolymph were applied to nitrocellulose paper using a Bio-Rad Bio-Dot SF microfiltration apparatus. A 2 µl sample of 3% (w/v) bovine serum albumin (BSA) served as a negative control, while 2 µl of *D. canadensis* hemolymph containing the THP was used as a positive control. The samples were probed with the anti-Dendroides THP antiserum, and antigen-antibody complexes were visualized with a horseradish peroxidase conjugated goat anti-rabbit IgG detection system using the protocol provided by the supplier (BioRad).

Immunofluorescence studies were also conducted to determine if THP was present in or on Lithobius gut cells. Cell preparations, some as collected from the field and others pretreated with THP and rinsed twice in buffer, were bathed for one hour in a solution of anti-Dendroides THP rabbit serum diluted 1:50 with PBS. After two additional PBS rinses the cells were bathed in a 1:3000 PBS dilution of goat anti-rabbit IgG fluorescent antibody (Biorad), held for one hour and rinsed twice more in PBS. Cells were then observed and photographed using a Nikon epifluorescent microscope. Negative controls consisted of cells treated as above but without either the anti-Dendroides THP rabbit serum (primary antibody) or the goat anti-rabbit fluorescent antibody (secondary antibody) treatments.

Results

The addition of THPs increased the survival of cells from freeze damage and in particular a THP concentration between 0.02 mg/ml ($2.4\times10^{-6}$M) and 0.20 mg/ml ($2.4\times10^{-5}$) was determined to be optimal. In the following examples a THP concentration of 0.02 mg/ml was used, unless otherwise indicated. It is noted that high concentrations of THP actually reduce cell survival upon freezing; a THP concentration of 2 mg/ml results in zero percent survivorship.

FIG. 5 demonstrates that addition of THPs had a positive effect on the survivorship of centipede gut cells subjected to freezing at various temperatures. FIG. 5a shows the linear decrease in survival rates obtained with decreasing freezing temperatures in gut cells from winter collected centipedes frozen without THPs. The $LT_{50}$ (the temperature at which 50% mortality occurred) was approximately −12.1° C. for this cell population. FIG. 5b shows a similar data set obtained from cells taken from summer animals, also frozen without THPs. The $LT_{50}$ was −8.2° C. for this cell population. The survival results for summer and for winter collected cells frozen in the presence of THPs are shown in FIGS. 5c and 5d, respectively. Note that addition of THPs improved the survivorship of these cells and that in the presence of THPs the freezing survival results are nearly identical for summer and winter collected cells, the $LT_{50}$'s being −15.0° and −15.1° C. respectively. Control trials of cells frozen with bovine serum albumin (BSA) showed that BSA had no effect on cell survival.

Figure 5A:
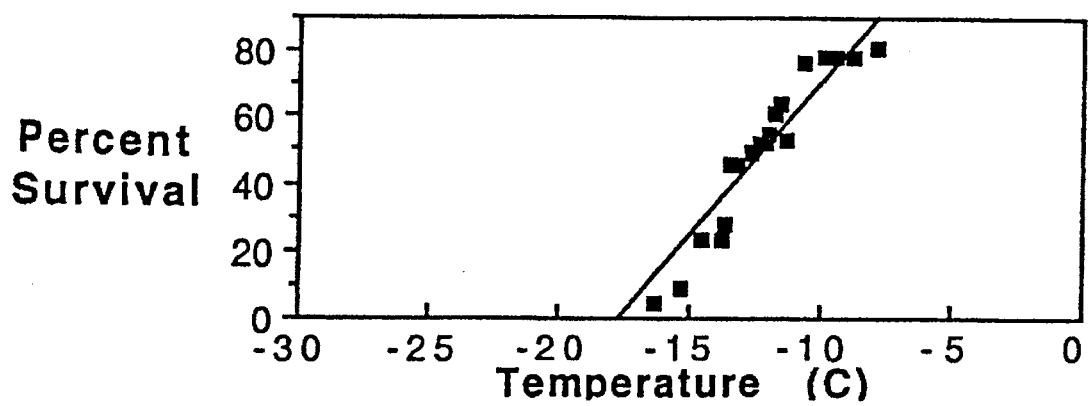
FIG. 5 is a graph illustrating the protective effect of *Dendroides canadensis* THPs to cells frozen under conditions designed to promote recrystalization.
Figure 5B:
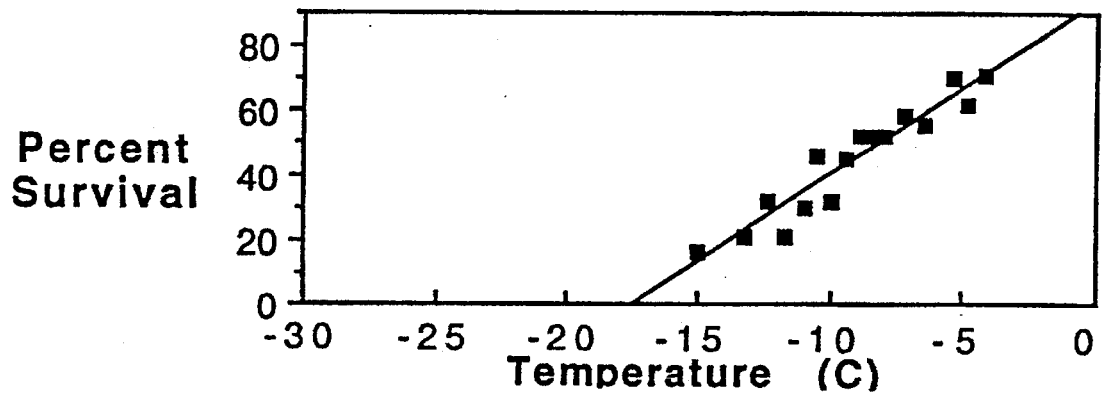
Figure 5C:
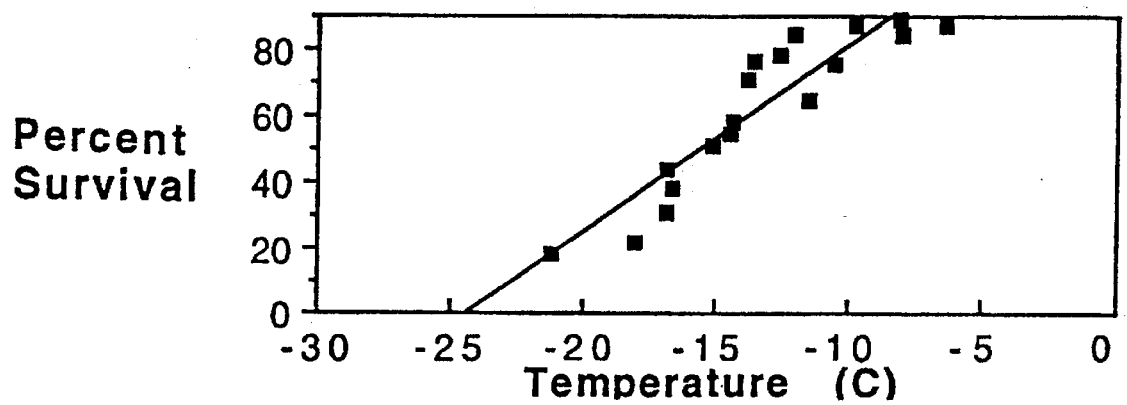
Figure 5D:
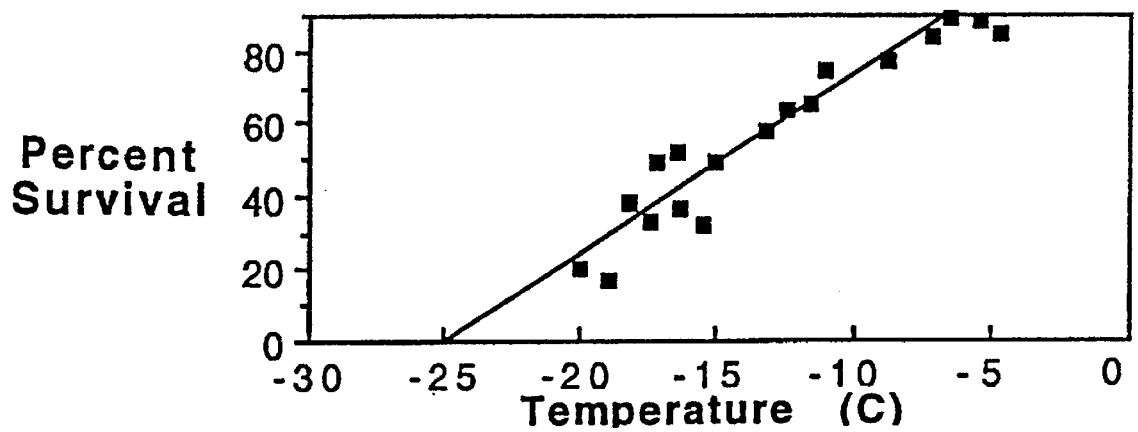
Figure 5E:
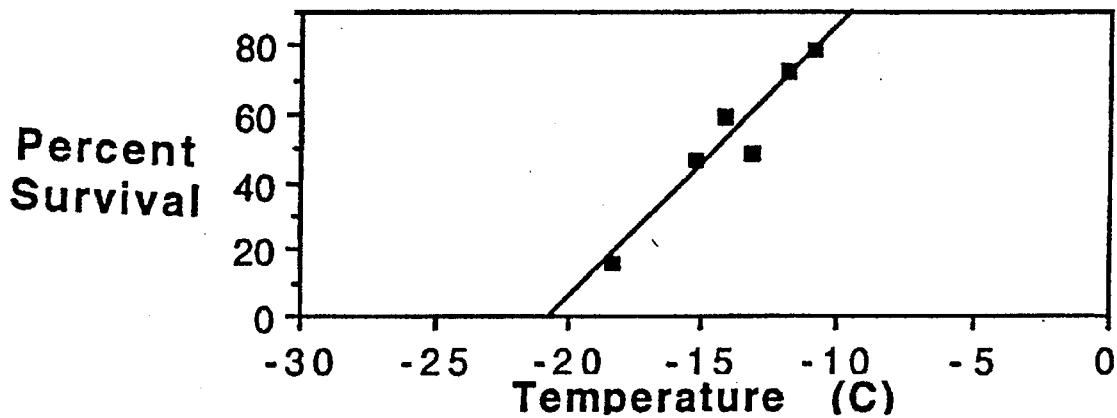

FIG. 5e demonstrates the effects of freezing at various temperatures on summer collected cells which had been equilibrated in a thermal hysteresis protein solution, rinsed twice to remove the protein from the bathing medium, and then frozen. The $LT_{50}$ was −14.5° C., comparable to that obtained when summer cells were frozen with THPs present in solution. This suggests that (1) some of the Dendroides THPs initially added to the bathing medium adhere to the cell membrane and are not washed off in the rinses and/or the THPs are incorporated into the cells; and (2) this THP provides protection from freezing. The adherence of THPs to cell membranes has been confirmed by immunofluorescent antibody test results.

Linear regression analysis of covariance demonstrated that the cells from winter collected individuals frozen without THPs had survival rates significantly different from those of cells collected in summer and frozen without THPs. The addition of Dendroides THPs significantly increased survivorship in both winter and summer collected cells, and summer cells treated with THPs exhibited survivorship which was not significantly different from that of winter cells treated with THPs. Also, the preparations of summer cells that were treated with protein and then rinsed showed survival rates that did not vary significantly from those of summer cells frozen in media containing THPs.

The positive effects of the addition of THPs on the survival rates of gut cells frozen under conditions designed to enhance recrystallization are summarized in Table 4. The survival rates of cells frozen without THPs under conditions designed to promote recrystallization are lower than those of cells frozen and held at a constant temperature of either −6° or −14° C. and then quickly thawed. The presence of THPs greatly improved survivorship of cells frozen under the recrystallization promoting scheme.

I claim:

1. A method for using a cell transformant comprising a heterologous DNA Sequence selected from the group consisting of Seq ID NO:1 and Seq ID NO:3 to produce a protein having antifreeze properties, said method comprising the step of culturing said cell transformant under conditions conducive to the expression of the antifreeze protein.

2. A isolated nucleic acid sequence comprising the sequence as set forth in Seq ID NO:1.

3. An isolated nucleic acid sequence comprising the sequence as set forth in Seq ID NO:3.

4. A polynucleotide sequence having a 20 base pair nucleotide portion identical in sequence to a consecutive 20 base pair portion of the sequence as set forth in Seq ID NO:1.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 525 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Dendroides canadensis ( x i ) SEQUENCE DESCRIPTION: SEQ ID NO:1:

| | | | | | | |
|---|---|---|---|---|---|---|
| GTTGAGTTGA | ACAAAATGGT | TTGGGTTTGC | AAAAATTCGA | TATTAGTAAT | TAGTGTAGTG | 6 0 |
| CTCATGTACG | TATGTCATGA | GTGTTATGGC | CAATGTACTG | GTGGTTCCGA | TTGTCGCTCG | 1 2 0 |
| TGTACAGTGT | CTTGTACTGA | CTGCCAGAAC | TGTCCAAATG | CACGTACAGC | ATGTACTCGC | 1 8 0 |
| TCTTCAAACT | GCATTAACGC | GTTAACCTGT | ACGGATTCAT | ATGATTGCCA | CAATGCCGAA | 2 4 0 |
| ACCTGTACTA | GATCAACCAA | TTGTTATAAG | GCTAAAACCT | GTACTGGATC | AACCAACTGT | 3 0 0 |
| TACGAAGCTA | CAGCCTGTAC | CGATTCCACG | GGATGTCCAT | GATCTTATTC | TATTCAGAGG | 3 6 0 |
| ATGAAGTACA | GGAGCGATAA | TAATTATTTT | ACTCATCAGA | TATATATGTT | TATTAATATT | 4 2 0 |
| AGAAATTATA | TGGAGTTAAA | TTAAACATGT | TTGATATCAT | GTTTGATATC | ATGTATTACG | 4 8 0 |
| GAACTCTAAA | TCAATACATA | TAAATAAAAT | AACATGTCAG | TAATA | | 5 2 5 |

( 2 ) INFORMATION FOR SEQ ID NO:2:

( i ) SEQUENCE CHARACTERISTICS:
        ( A ) LENGTH: 108 amino acids
        ( B ) TYPE: amino acid
        ( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
        ( A ) ORGANISM: Dendroides canadensis ( x i ) SEQUENCE DESCRIPTION: SEQ ID NO:2:

|  | Met<br>1 | Val | Trp | Val | Cys<br>5 | Lys | Asn | Ser | Ile | Leu<br>10 | Val | Ile | Ser | Val | Leu<br>15 |
|---|---|---|---|---|---|---|---|---|---|---|---|---|---|---|---|
|  | Met | Tyr | Val | Cys<br>20 | His | Glu | Cys | Tyr | Gly<br>25 | Gln | Cys | Thr | Gly<br>30 | Gly | Ser | Asp |
|  | Cys | Arg | Ser<br>35 | Cys | Thr | Val | Ser | Cys<br>40 | Thr | Asp | Cys | Gln | Asn<br>45 | Cys | Pro | Asn |
|  | Ala | Arg<br>50 | Thr | Ala | Cys | Thr | Arg<br>55 | Ser | Ser | Asn | Cys | Ile<br>60 | Asn | Ala | Leu | Thr |
|  | Cys<br>65 | Thr | Asp | Ser | Tyr | Asp<br>70 | Cys | His | Asn | Ala | Glu<br>75 | Thr | Cys | Thr | Arg | Ser<br>80 |
|  | Thr | Asn | Cys | Tyr | Lys<br>85 | Ala | Lys | Thr | Cys | Thr<br>90 | Gly | Ser | Thr | Asn | Cys<br>95 | Tyr |
|  | Glu | Ala | Thr | Ala<br>100 | Cys | Thr | Asp | Ser | Thr<br>105 | Gly | Cys | Pro |  |  |  |  |

(2) INFORMATION FOR SEQ ID NO:3:

(i) SEQUENCE CHARACTERISTICS:
        (A) LENGTH: 487 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Dendroides canadensis (xi) SEQUENCE DESCRIPTION: SEQ ID NO:3:

| CGAGCAGTTG | AGTTGAACAA | AATGGTTTGG | GTTTGCAAAA | GTTCGATATT | AGTAATTAGT | 60 |
|---|---|---|---|---|---|---|
| GTAGTTCTCA | TGTACGTATG | TCATGAGTGT | TATGGCCAAT | GTACTGGTGG | TTCCGATTGT | 120 |
| CGCTCGTGTA | CAGTGTCTTG | TACTGACTGC | CAGAACTGTC | CAAATGCACG | TACAGCATGT | 180 |
| ACTCGCTCCT | CAAACTGCAA | CAACGCGTTA | ACTTGTACGG | ATTCATATGA | TTGCCACAAT | 240 |
| GCCGAAACCT | GTACTAGATC | AACCAATTGC | TATAAGGCCA | AAACCTGTAC | TGGATCAACC | 300 |
| AACTGTTACG | AAGCTACTAC | AGCCTGTACC | GATTCCACGG | GATGTCCATG | ATCTTATTCT | 360 |
| ATTCAGAGGA | TGAAGTACAG | GAGCGATGAT | AATAATTATT | TTACTCATCA | CATATATATG | 420 |
| TTTATTAATA | TTAGAAATTA | TATGGAGTTA | AATTAAACAT | GTATAACATG | TTTGATATCA | 480 |
| TATATAC |  |  |  |  |  | 487 |

(2) INFORMATION FOR SEQ ID NO:4:

(i) SEQUENCE CHARACTERISTICS:
        (A) LENGTH: 109 amino acids
        (B) TYPE: amino acid
        (D) TOPOLOGY: linear (ii) MOLECULE TYPE: protein (iii) HYPOTHETICAL: YES (iv) ANTI-SENSE: NO (vi) ORIGINAL SOURCE:
        (A) ORGANISM: Dendroides canadensis (xi) SEQUENCE DESCRIPTION: SEQ ID NO:4:

|  | Met<br>1 | Val | Trp | Val | Cys<br>5 | Lys | Ser | Ser | Ile | Leu<br>10 | Val | Ile | Ser | Val | Leu<br>15 |
|---|---|---|---|---|---|---|---|---|---|---|---|---|---|---|---|

| | | | | | | | | | | | | | | | |
|---|---|---|---|---|---|---|---|---|---|---|---|---|---|---|---|
|Met|Tyr|Val|Cys<br>20|His|Glu|Cys|Tyr|Gly<br>25|Gln|Cys|Thr|Gly|Gly<br>30|Ser|Asp|
|Cys|Arg|Ser<br>35|Cys|Thr|Val|Ser|Cys<br>40|Thr|Asp|Cys|Gln|Asn<br>45|Cys|Pro|Asn|
|Ala|Arg<br>50|Thr|Ala|Cys|Thr|Arg<br>55|Ser|Ser|Asn|Cys|Asn<br>60|Asn|Ala|Leu|Thr|
|Cys<br>65|Thr|Asp|Ser|Tyr|Asp<br>70|Cys|His|Asn|Ala|Glu<br>75|Thr|Cys|Thr|Arg|Ser<br>80|
|Thr|Asn|Cys|Tyr|Lys<br>85|Ala|Lys|Thr|Cys|Thr<br>90|Gly|Ser|Thr|Asn|Cys<br>95|Tyr|
|Glu|Ala|Thr|Thr<br>100|Ala|Cys|Thr|Asp|Ser<br>105|Thr|Gly|Cys|Pro| | | |

( 2 ) INFORMATION FOR SEQ ID NO:5:

( i ) SEQUENCE CHARACTERISTICS:
        ( A ) LENGTH: 39 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: YES ( i v ) ANTI-SENSE: NO ( v i ) ORIGINAL SOURCE:
        ( A ) ORGANISM: Dendroides canadensis ( x i ) SEQUENCE DESCRIPTION: SEQ ID NO:5:

TGYYNYRMNK SNNNWRNNNN NTGTACNNRN TSNWMNRWY        39

( 2 ) INFORMATION FOR SEQ ID NO:6:

( i ) SEQUENCE CHARACTERISTICS:
        ( A ) LENGTH: 36 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: YES ( i v ) ANTI-SENSE: NO ( v i ) ORIGINAL SOURCE:
        ( A ) ORGANISM: Dendroides canadensis ( x i ) SEQUENCE DESCRIPTION: SEQ ID NO:6:

TGYNNNAANG CNNNAACNTG TACNNRNTCA WMNRWY        36

( 2 ) INFORMATION FOR SEQ ID NO:7:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

(A) ORGANISM: Dendroidies canadensis (xi) SEQUENCE DESCRIPTION: SEQ ID NO:7:

```
Asp Cys Val Asn Cys Pro Asn Ala Leu Thr Ala Cys Thr Arg Ser Thr
1               5                   10                  15
Asn Cys Tyr Lys Ala Val Thr Cys Thr Lys Ser Tyr
                20                  25
```

(2) INFORMATION FOR SEQ ID NO:8:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (iii) HYPOTHETICAL: YES (iv) ANTI-SENSE: NO (v) FRAGMENT TYPE: internal (vi) ORIGINAL SOURCE:
        (A) ORGANISM: Dendroides canadensis (xi) SEQUENCE DESCRIPTION: SEQ ID NO:8:

```
Cys Xaa Xaa Ala Xaa Thr Xaa Cys Thr Xaa Ser Xaa Asx
1               5                   10
```

(2) INFORMATION FOR SEQ ID NO:9:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (iii) HYPOTHETICAL: YES (iv) ANTI-SENSE: NO (v) FRAGMENT TYPE: internal (vi) ORIGINAL SOURCE:
        (A) ORGANISM: Dendroides canadensis (xi) SEQUENCE DESCRIPTION: SEQ ID NO:9:

```
Cys Xaa Xaa Ala Xaa Thr Cys Thr Xaa Ser Xaa Asx
1               5                   10
```